United States Patent [19]

Crawford et al.

[11] Patent Number: 4,578,753

[45] Date of Patent: Mar. 25, 1986

[54] SYSTEMS AND METHODS FOR MINIMIZING NONCOPLANARITY ARTIFACTS

[75] Inventors: Carl R. Crawford, Milwaukee, Wis.; Yair Shimoni, Jerusalem, Israel; A. Robert Sohval; Daniel I. Barnea, both of Brookline, Mass.

[73] Assignee: Elscint Ltd., Haifa, Israel

[21] Appl. No.: 527,472

[22] Filed: Aug. 29, 1983

[51] Int. Cl.[4] .............................................. G06F 15/42
[52] U.S. Cl. ..................................... 364/414; 378/11; 378/901
[58] Field of Search .............. 364/413, 414, 415, 416, 364/417; 358/111, 903; 378/98–100, 21, 23–27, 901, 4, 11, 14

[56] References Cited

U.S. PATENT DOCUMENTS

| | | | |
|---|---|---|---|
| 4,145,613 | 3/1979 | Bunch | 378/26 X |
| 4,147,936 | 4/1979 | Eickel | 378/27 X |
| 4,178,511 | 12/1979 | Hounsfield et al. | 364/414 X |
| 4,222,104 | 9/1980 | Moore | 364/414 |
| 4,266,136 | 5/1981 | Duinker | 250/445 T |
| 4,272,820 | 6/1981 | Lux | 364/414 |
| 4,293,912 | 10/1981 | Walters | 364/414 |
| 4,313,163 | 1/1982 | Mizutani | 364/414 |
| 4,418,387 | 11/1983 | Yamaguchi et al. | 364/414 |
| 4,472,823 | 9/1984 | Waltham | 378/901 X |
| 4,482,958 | 11/1984 | Nakayama et al. | 364/414 |

OTHER PUBLICATIONS

Parker, D. L., "Optimal Short Scan Convolution Reconstruction for Fanbeam CT", Med. Phys., vol. 9, No. 2, Mar. 1982, pp. 254–258.

Boyd, D. P., "Theoretical Possibilities for CT Scanner Development", Diagnostic Imaging, Dec. 1982.
Robb, R. A., "X-Ray Computed Tomography: an Engineering Synthesis of Multi-Scientific Principles", and Critical Reviews in Biomedical Engineering, Ed., J. R. Bourne, CRC Press, Mar. 1982, pp. 265-327.
Kuhl, D. E. and Edwards, R. Q., "Reorganizing Data from Transverse Section Scans of the Brain Using Digital Processes", Radiology, vol. 91, pp. 975-983, Nov. 1968.
A. Zenari, J. W. Scrimger and R. Hooper, "An Assessment of the Physical Properties of a Multiplane Tomographic Imager," *Phys. Med. Biol.*, 1983, vol. 28, No. 11, pp. 1235-1249.

Primary Examiner—Gary V. Harkcom
Attorney, Agent, or Firm—Sandler & Greenblum

[57] ABSTRACT

The system and method of the present invention minimizes artifacts caused by noncoplanarity between source and detector component in a computerized tomography system. The source component produces a beam of penetrating radiation which is rotatable about an axis and is incident on the detector component; and non-coplanarity is defined by the collection of the positions of the source component which defines a first plane, and by the collection of positions of the detector component which defines a second plane axially spaced from the first plane. Data obtained during a scan of a body located between the source and detector components are processed to form two images, one image being based on data related to one side of a focal plane interposed between the first and second planes, and another image being based on data related to the other side of the focal plane.

20 Claims, 5 Drawing Figures

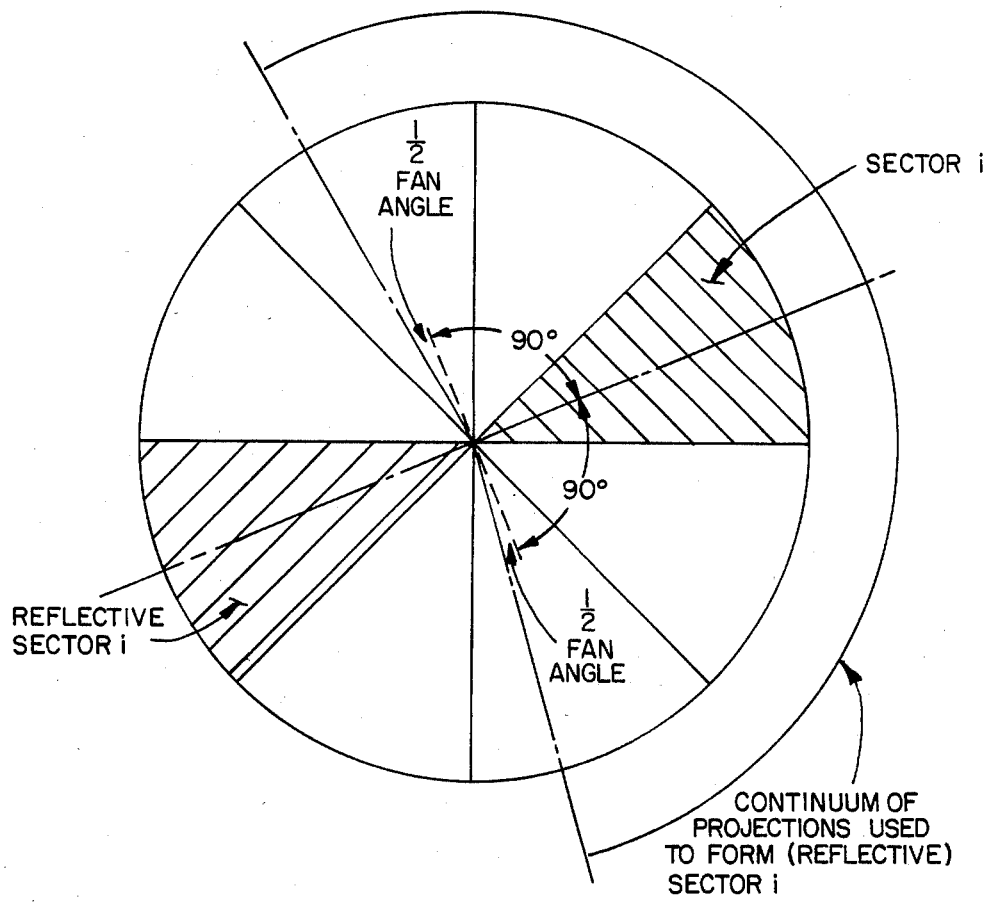

SYSTEMS AND METHODS FOR MINIMIZING NONCOPLANARITY ARTIFACTS

FIELD OF THE INVENTION

This invention is concerned with computerized tomography and more particularly with systems for eliminating or at least minimizing artifacts caused by a lack of planarity between the detector means and the radiation source means in the gantry of CT scanners.

BACKGROUND OF THE INVENTION

The evolution x-ray computed tomography (CT) has produced scanners with decreasing data acquisition and image reconstruction times and improved density and spatial resolutions. The improvements have been achieved primarily by the use of more sophisticated data acquisition systems and faster image reconstruction hardware. The image quality has also been improved by reevaluating assumptions used in the algorithms of the early generations of CT scanners and by incorporating corrections and/or refinements of these assumptions within the image reconstruction algorithm.

The assumptions were initially made to assure the compatability of the real data collected by an actual scanner with theoretical reconstruction algorithms which for example require an infinite number of line-integral values of the two-dimensional attenuation function. In reconstruction algorithms, the line-integral values are inverted resulting in two-dimensional object density functions which are presented to the user as images.

CT scanners employ a plurality of source means and a plurality of detector means which are each provided with a scanning movement, relative to a body, to provide a measure of attenuation for each of a plurality of straight line radiation connecting the source means to the detector means. Those attenuation measurements are then processed by suitable means to provide a distribution of line-integral values of object density function. To provide the required plurality of line-integrals, the source and detectors are moved in predefined patterns.

In a translate-rotate system, assuming the source emits a fan-beam formed of a plurality of pencil beams, the detectors, during translation, provide information relevant to a plurality of sets of parallel beam paths. The sets are angularly spaced by the angular separation of the beams. Each pencil beam, in the course of the lateral scan, provides the data for a set of parallel beam paths. Data from each such parallel set is processed to give parallel projections of the object density function. Usually, filtered backprojection methods are used to reconstruct the density function from the parallel projections collected over a minimum of 180 degrees of rotation.

In rotate-rotate scanners, in which the source and detectors are fixed in relation to one another and rotate together around the object, it is customary to convert the non-parallelized data collected thereby into parallel data format by a suitable resorting or re-binning technique. This is because conventional backprojection methods are adapted to the parallelized data produced by a translate-rotate type scanner. Re-binning or resorting techniques have been disclosed in the U.S. Pat. No. 4,266,136. The resorting algorithm requires a rotation angle of 180 degrees plus the angle subtended by the source-fan. Methods are also available for directly reconstructing the fan-beam data required by the resorting algorithm. This method is outlined in the paper: D. L. Parker, "Optimal Short Scan Convolution Reconstruction for Fanbeam CT," Medical Physics, Vol. 9, No. 2, March 1982, pp. 254–258.

Most of the presently available CT scanners use what can be referred to as coplanar source-detector configurations. That is, the centers of apertures of all the detector- and the source-positions are in the same plane known as the scan plane. This two-dimensional configuration is the result of the mathematics of conventional reconstruction theory that require all line-integrals of the density function to lie in a plane.

A major problem with actual CT scanners is that the detector and source means have apertures that extend in the axial direction; i.e., perpendicular to the scan plane. Implicit to the image reconstruction algorithm is the assumption that the object is spatially invariant in the axial direction. This assumption is seldom satisfied. Thus, what are known as "partial volume" artifacts are present in the final reconstruction of the scan plane. In order to reduce partial volume artifacts, the heights of the source and detector apertures in the axial direction are made as small as possible.

In some CT scanners the source and the detector apertures are intentionally designed to be in separate planes. Such machines are described as having noncoplanar configurations. Noncoplanar machines have been described in the following articles: D. P. Boyd, "Theoretical Possibilities for CT Scanner Development," Diagnostic Imaging, Dec. 1982; R. A. Robb, "X-ray Computed Tomography: An Engineering Synthesis of Multiscientific Principles," in "Critical Reviews in Biomedical Engineering," Ed. J. R. Bourne, CRC Press, March 1982, pp. 265–327. A consequence of this new noncoplanar geometry is that the partial volume artifacts will be enhanced. This new level of partial volume artifacts are denoted as "noncoplanarity artifacts".

Noncoplanarity causes several different types of artifacts of which two are of primary concern. The first is related to axial resolution and the other is related to inconsistencies in the data interacting with the reconstruction algorithm.

The slice-volume of a scanner is the volume formed by the collection of all of the paths taken by the line-integral values. The slice-volume in the noncoplanar geometry is much larger and more irregular than the slice-volume in the coplanar geometry. Because objects have spatial variations in the axial direction, the axial resolutions of noncoplanar machines are significantly less than in corresponding coplanar scanners.

The second type of artifact caused by noncoplanarity is a result of inconsistencies in the measured line integral data. All present reconstruction algorithms assume or require that line integrals along two opposite paths be identical. However, if there is any variation of the object's attenuation coefficient in the axial direction, the line-integrals along the two opposite paths in the noncoplanar configuration will not be identical. The effect of this inconsistency is to cause artifacts in reconstructed images. Because of the physical shape and density distribution of the artifacts, they are called "butterfly artifacts."

If scanners with noncoplanar geometries are ever expected to produce valuable images, the large slice volume and the "butterfly artifacts" must be reduced. Since there always exists a degree of noncoplanarity, there is always a point at which the noncoplanarity artifacts will make the images clinically unusable. Thus, there exists the need for systems and methods to correct for noncoplanarity artifacts.

BRIEF DESCRIPTION OF THE INVENTION

According to a broad aspect of the invention, a correction method is provided for minimizing artifacts caused by one type of noncoplanarity between source means and detector means in computerized tomography, said noncoplanarity defined by the collection of the positions of said source means describing a first plane, the collection of the positions of said detector means describing a second plane axially removed from and parallel to said first plane, said method comprising the steps of:

energizing said source means to provide radiation extending from said source means to said detector means through an object, detecting said radiation and forming line-integrals of the attenuation coefficients of the object, forming the data into 360 degrees of projections, filtering the collected data, and reconstructing two images by reconstructing a finite number of radial lines twice, once using the minimum filtered projection data required by the reconstruction algorithm centered about the angle of a radial line, the second time with the filtered projection data centered about the angle of a radial line plus 180 degrees.

According to a feature of the present invention, the method includes the step of:

forming the two reconstructions of the radial lines that comprise an image simultaneously. The result of the described method is the production of two distinct images representing the upper and lower sections of the slice volume. The use of the two images significantly improves the axial resolution and reduces the "butterfly artifacts" that are a characteristic of noncoplanarity.

The above method implicitly is optimized for data originating from a translate-rotate CT scanner also known as first- or second-generation machines. However, it is possible to resort or rebin data from any machine configuration to cause the data to look like the data collected from the translate-rotate configuration. Thus, the inventive method features the additional step of:

resorting the data obtained from an arbitrary configuration into parallel projection data and proceeding as outlined above.

Another feature of the invention further contemplates a more generalized method for treating data to correct for noncoplanarity. Resorting often requires the use of interpolation such as in the use of rotate-rotate scanners. Interpolated values are not necessarily consistent and therefore resorting often produces streak artifacts in the reconstructions. Thus, this interpolation step may introduce artifacts which are worse than the original noncoplanarity artifacts. Therefore, a direct back-projection algorithm (without interpolation to parallel projection data) is provided in the prior art that is designed for the specific geometry when obtaining the data from a scanner with a rotate-rotate configuration. Another method which is within the scope of this invention uses fan-beam projection data obtained directly from the rotate-rotate scanner in place of the parallel projections; the method includes the steps of:

dividing the image into thick wedge-like spokes and proceeding with the above outlined method by treating the wedges as the radial lines.

BRIEF DESCRIPTION OF THE DRAWINGS

The above noted and other features and objects of the invention will be best understood when considered in accordance with the following description made in conjunction with the accompanying drawings, wherein:

FIG. 5 is a pictorial showing of a thick wedge-like spoke used with fan-beam configurations in accordance with the invention.

GENERAL DESCRIPTION

Figure 1:
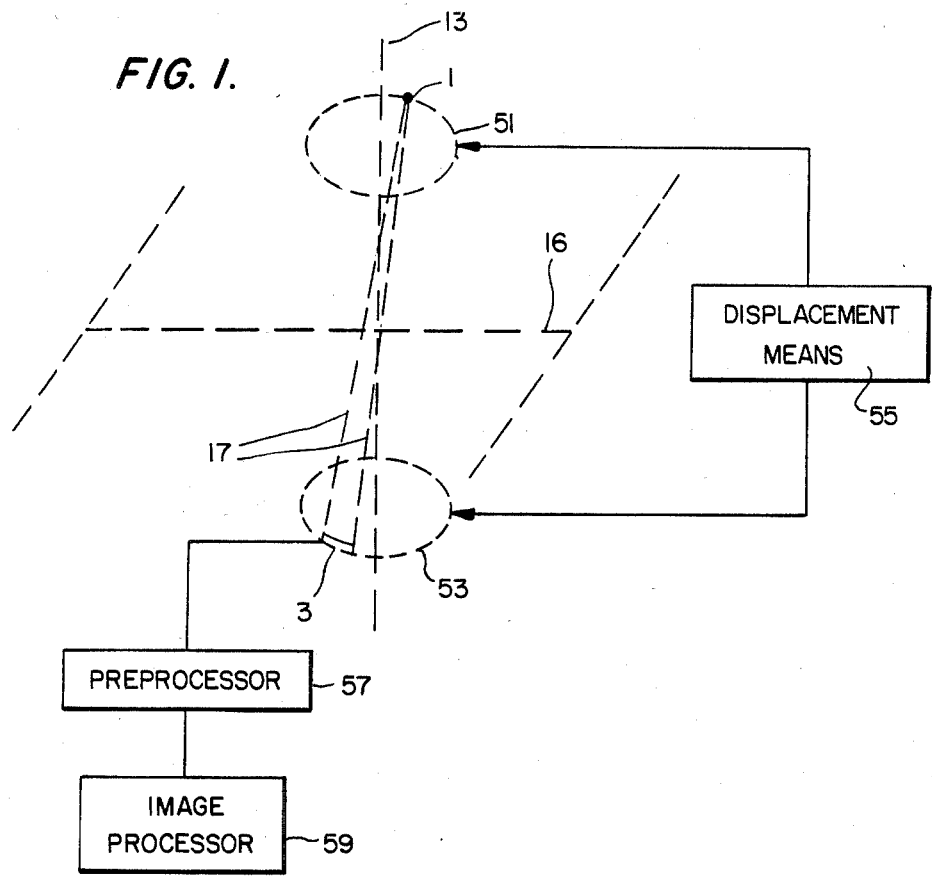
FIG. 1 is a partial block diagram which illustrates a noncoplanar source detector cofiguration according to the present invention.

Referring now to FIG. 1, reference numeral 1 refers to source means for emitting radiation beams through a body which is located between detector means 3 and source means 1 in the region of axial axis 13. Detector means 3 is disposed in a plane which is distinct from and substantially parallel to a plane in which source means 1 is disposed. Detector means 3 receives radiation beams from source means 1 which produce intensity signals representing the intensity of beams which are passed through the body under examination. The output of detector means 3 is passed to preprocessing unit 57 which produces projection data representing line-integrals though the body under investigation. The line-integral data is passed to image processing unit means 59 which produces a plurality of images representing the body under investigation.

In FIG. 1, a rotate-rotate system is shown, wherein source means 1 is rotated around axis 13 along dashed circular line 51, while detector means 3 is rotated around dashed circular line 53, source means 1 and detector means 3 being fixed in relation to one another. It should be noted that the present invention is not limited to a rotate-rotate configuration, but that in addition, other CT configurations can be employed, such as translate-rotate, rotate-stationary, or fully stationary strobed source configurations. Of course, it is to be understood that source means 1 and detector means 3 are both mounted on a suitable support member (not shown).

In FIG. 1, reference numeral 17 represents a radiation beam emitted by source means 1 which is incident on detector means 3. Reference numeral 16 refers to a focal-plane which lies parallel to and is located approximately midway between the respective planes in which source means 1 and detector means 3 are disposed. Displacement means 55 causes source means 1 to emit radiation from a plurality of locations to provide a full 360 degrees of parallel projection signals with respect to the body under examination for a translate-rotate system or a full 360 degrees of fan-beam data with respect to the body for a rotate-rotate system. It should be noted that displacement means 55 causes both source means 1 and detector means 3 to rotate in tandem in a rotate-rotate system, but causes only source means 1 to rotate in a rotate-stationary system. Further, in a translate-rotate system, displacement means 55 would both translate and rotate both source means 1 and detector means 3 with respect to the body.

Figure 2:
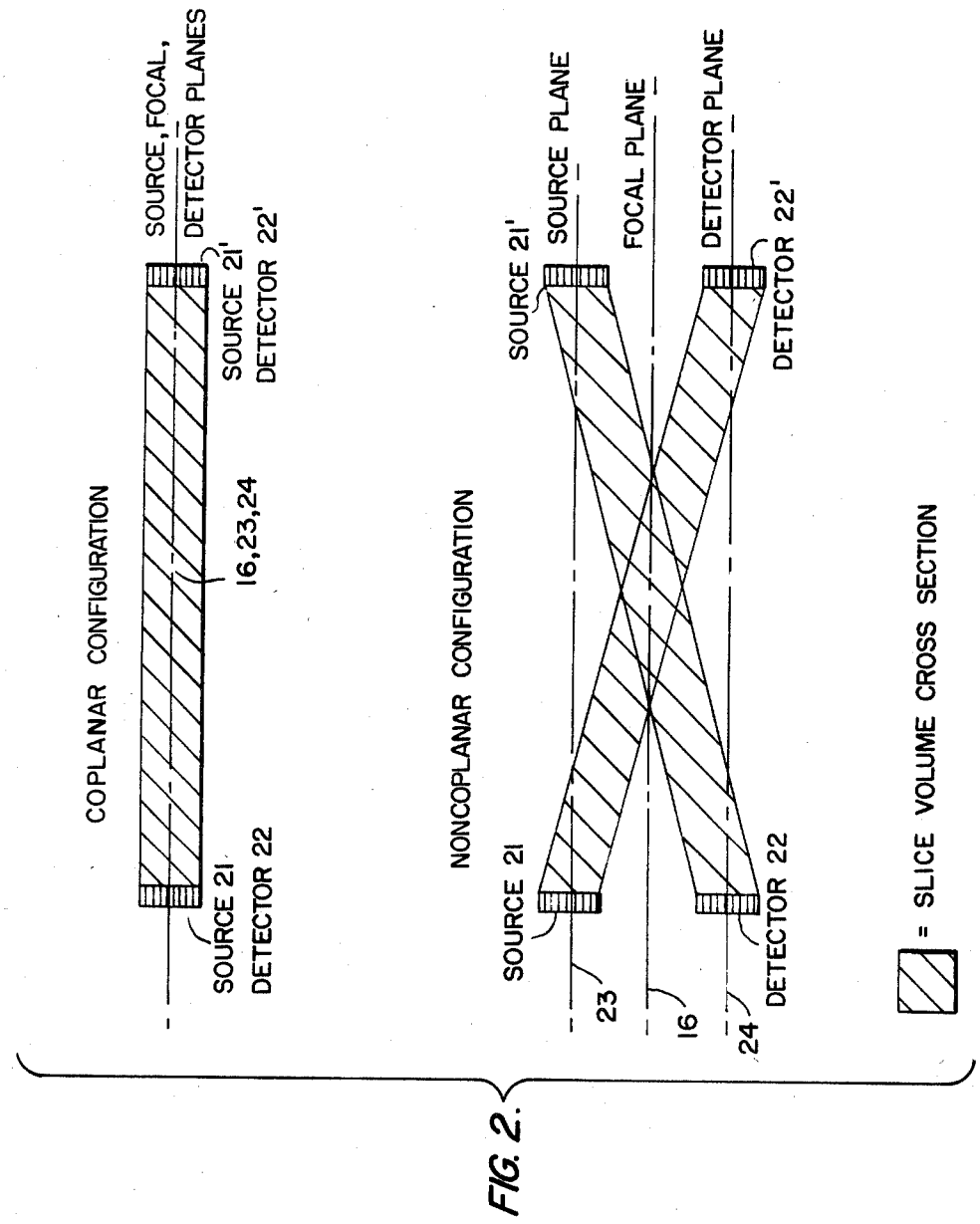
FIG. 2 is a pictorial showing a cross-section of coplanar and noncoplanar source detector configurations.

In the generally available CT scanners there is ideally coplanarity, as shown in the top portion of FIG. 2, between the centers of all of the apertures of the source means and the detector means. A source of radiation such as X-ray tube 21 is on the same plane as a detector 22. When the source/detector pair rotates through 180 degrees to the positions 21' and 22', respectively, the same path connects the centers of the source and detector apertures.

The bottom portion of FIG. 2 shows, by way of contrast, source and detector means that are not coplanar. The source means lie in the source plane 23 and the detector means lie in the detector plane 24. The plane centered between the source and detector planes is called the focal plane and is denoted 16 in FIG. 2. As shown in FIG. 2B, when the source 21 moves to position 21' and detector 22 moves to 22', a path connecting the centers of the apertures of the source means and the detector means is different from the original connecting path.

The inconsistencies in the paths described above lead to the above mentioned butterfly artifacts. The noncoplanarity of the source and detector means leads to decreased resolution in the axial direction. The unique methods used to reduce the effects of noncoplanarity will be better understood by examining the following mathematics pertaining to reconstruction theory.

Consider function f(x,y) which represents a cross-section of an object and the path characterized with ($\theta$,t) given by:

$$t = x^* \cos(\theta) + y^* \sin(\theta). \tag{1}$$

A sample, p($\theta$,t), of the projection of the object function along the path characterized with ($\theta$,t), is given by:

$$p(\theta,t) = \int\int f(x,y)\, \delta(t - x^* \cos(\theta) - y^* \sin(\theta))dxdy, \tag{2}$$

where $\delta(z)$ is described by the following integral equation:

$$\int \delta(z)g(z)dz = g(0). \tag{3}$$

The projection of an object is obtained in the manner well known to those skilled in the art.

Filtered object projections are given by:

$$q(\theta,t) = p(\theta,t) <^*> h(t), \tag{4}$$

where the operation of convolution is denoted by $<^*>$ and h(t) is one of the well known filtering functions required by backprojection algorithms.

In prior art equipment, the backprojection operation used for reconstructing the object f(x,y) is described by:

$$f(x,y) = \int q(\theta, x^* \cos(\theta) + y^* \sin(\theta))d\theta, \tag{5}$$

where the limits in the integral are over any range of $\theta$ that has an extent of 180 degrees. However, the range is fixed for all values of 'x' and 'y'.

Let F($\phi$,$\rho$) be the polar-coordinate representation of the object function f(x,y). The two functions can be related as follows:

$$f(x,y) = F(\phi,\rho), \tag{6}$$

for $$x = \rho^* \cos(\phi), \tag{7a}$$

$$y = \rho^* \sin(\phi), \tag{7b}$$

where $$0 <= \rho < \infty.$$

The reconstruction integral can be expressed in polar-coordinates if (6) and (7) are substituted into (5):

$$F(\phi,\rho) = \int q(\theta,\rho^* \cos(\theta - \phi))d\theta, \tag{8}$$

where it is emphasized that $\phi$ takes all values between zero and $2\pi$ and $\rho$ is non-negative.

Consider a radial line of 'f' at $\phi$. It is easy to see from the geometry of the noncoplanar configuration that p($\phi$, 0) will have its largest contributions from objects along the radial line at $\phi$ that lie above the focal-plane and by objects that lie below the focal-plane along the radial line and $\phi + \pi$. Thus an optimized reconstruction of the radial line corresponding to the slice-volume above the focal-plane can be given by:

$$F(\phi,\rho) = \int_{\phi - \pi/2}^{\phi + \pi/2} q(\theta,\rho^* \cos(\theta - \phi))d\theta. \tag{9}$$

It is easy to extend the above argument to show that p($\phi + \pi$, 0) has its largest contributions from objects that lie below the focal plane for the line characterized by $\phi$ and for objects along the radial line characterized with $\phi + \pi$ that lie above the focal plane. Thus an optimized reconstruction of the radial line corresponding to the slice-volume below the focal-plane can be given by:

$$F(\phi,\rho) = \int_{\phi + \pi/2}^{\phi + 3^*\pi/2} q(\theta,\rho^* \cos(\theta - \phi))d\theta. \tag{10}$$

Because every image is a collection of 360 degrees of radial lines, the integral equations in (9) and (10) can be used to reconstruct two images. The result of the described method is the production of the two distinct images representing the upper and lower sections of the slice volume. The two images significantly improve axial resolution and reduce the "butterfly artifacts" that are a characteristic of noncoplanarity.

Figure 3:
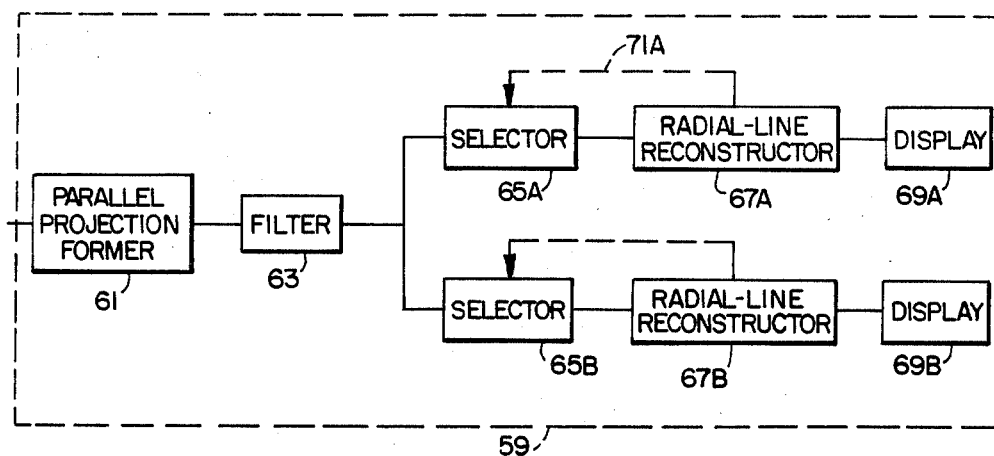
FIG. 3 is an expanded block diagram of the image processing means shown in FIG. 1.

A system used to implement the above method is shown in FIG. 3, wherein an expanded diagram of image processing means 59 is shown. Parallel projection forming means 61 generates 360 degrees of parallel projection data. The output of 61 is passed to filtration means 63. Reconstruction means 67 generates an image from the filtered projection data by reconstructing the images by collecting the reconstructions of a series of radial lines. The data used by the reconstruction means 67 is selected by selection means 65. The selection means 65 select data as a function of the current radial line being reconstructed by reconstruction means 67. Selection means 65a is designed to select projection data centered at the angle of the radial line and selection means 65b is designed to select data centered at the angle of the radial line plus 180 degrees. Feedback means 71 provides the angle of the radial line being reconstructed by reconstruction means 67 to the selection means 65. The resulting images are displayed on image display means 69.

The integrals in (9) and (10) are in the standard form of backprojection integrals. It is easy to extend the normal backprojection method to incorporate the dual-image method described above. This is because every radial-line is reconstructed using 180 degrees of filtered projections.

Figure 4:
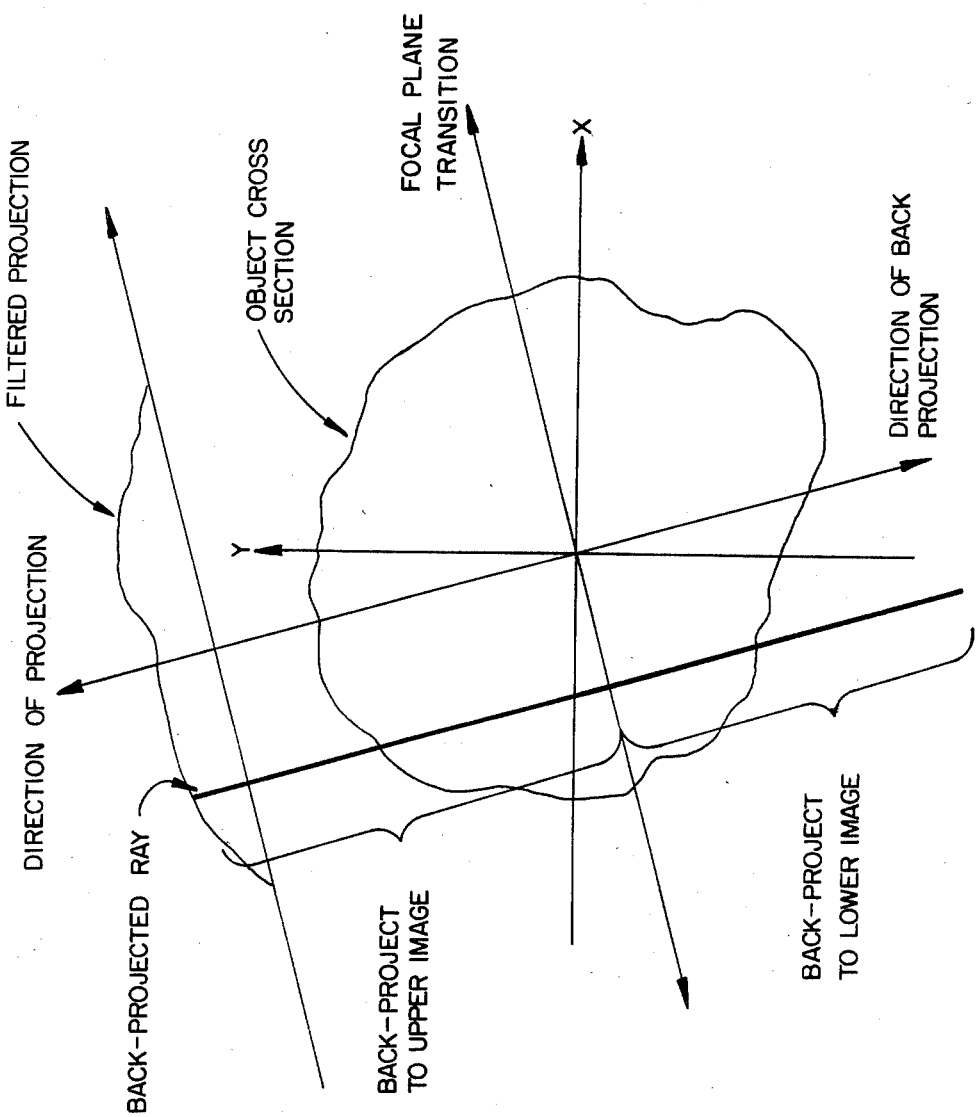
FIG. 4 is a pictorial showing of the partitioning of the back projection into upper and lower images, in accordance with the invention.

The extended method is presented in FIG. 4. The method consists of the following steps:
forming 360 degrees of parallel projections,
filtering the parallel projections,
presetting to zero an image representing the upper-volume and an image representing the lower volume, and
backprojecting all 360 degrees of filtered projections, said backprojection step is modified so that a projection is backprojected into the upper image for all pixel values before the focal-plane transition and into to the lower image after the focal-plane transition, wherein said focal-plane transition is the straight line intersecting the scan origin at an the same angle as the projection currently being backprojected.

The method results in circular artifacts because of the "sharp" transition when the switch is made between the images when the focal-plane transition is crossed. The circle artifacts connect high density objects with the origin of scan plane. These circle artifacts can be reduced by smoothing the transition around the focal plane. The smoothing procedure is implemented by backprojecting into both images for a region near the focal-plane transition. However, the values backprojected in this region are weighted so that the sum of the contribution of a given projection and the contribution from the projection displaced by exactly 180 degrees from the given projection is exactly one.

The above described procedures can be generalized because, from a mathematical viewpoint, the data collected in the translate-rotate configuration is identical to the data collected in any other reconstructable configuration. It is always possible to rebin or resort data to conform to data from the translate-rotate mode. Once the resorting is accomplished the previously described procedure can be used to correct for noncoplanarity.

Resorting often requires the use of interpolation such as in the use of rotate-rotate scanners. Interpolated values are not necessarily consistent and therefore resorting often generates streak artifacts in the reconstructions. Thus, this interpolation step may introduce artifacts which are worse than the original noncoplanarity artifacts. Therefore, it is desired to extend the above methods to the case of rotate-rotate scanner without using the step of resorting.

Note that in the method of correcting for noncoplanarity described with respect to FIG. 4, each of the two surface reconstructions receives contributions from 180 degrees of filtered projections instead of from all 360 degrees. Note that the method of FIG. 4 is a fast algorithm for all pixels in both images. The FIG. 4 algorithm is not directly applicable, however, to the rotate-rotate data because projections are needed from 180 degrees plus the fan-angle. In addition, the projections are weighted prior to filtration with a function dependent on the angle of a projection.

The direct analogy of the algorithm of FIG. 4 to fan beam data is to reconstruct each radial line in each of the upper and lower image independently of the other radial lines. Each radial line is obtained using a direct 180 degree plus fan beam reconstruction algorithm. This algorithm is very time-consuming. The solution is to take some short-cuts as illustrated in FIG. 5 where, in effect, "fat" radial lines are depicted by the use of sectors.

The 360 degrees of fan beam projection data is divided into K overlapping sets of data; each covering 180 degrees plus the fan angle. For each set, reconstruct a sector centered within the data. Also, immediately reconstruct the sectors' reflection. Combine the K sectors to form the upper surface and combine the reflective sectors to form the lower surface. The overlapping sectors are used to smooth the transitions across sector boundaries.

While the invention has been described in relation to specific procedures and embodiments, it should be understood that this description is by way of example and not meant as a limitation on the scope of the invention.

What is claimed is:

1. A correction method for minimizing artifacts caused by noncoplanarity between source means and detector means in computerized tomography, wherein said source means produces a beam of penetrating radiation which is rotatable about an axis and is incident on said detector means, whereby said noncoplanarity is defined by the collection of the positions of said source means which defines a first plane, and by the collection of the positions of said detector means which defines a second plane axially displaced from said first plane, said method including the steps of:
  (a) energizing said source means to provide radiation that passes from said source means to said detector means through an object when the latter is located between said source means and said detector means whereby output signals from the detector means are obtained;
  (b) processing said output signals to form representations of line-integrals of the attenuation coefficients of the object;
  (c) processing said representations into filtered projection data over 360 degrees,
  (d) filtering the projection data; and
  (e) reconstruction two images by twice reconstructing a finite number of radial lines using a reconstruction algorithm, one reconstruction using the minimum filtered projection data required by the reconstruction algorithm centered about the angle of each radial line, and another reconstruction using the filtered projection data centered about the angle of the radial line plus 180 degrees.

2. The method of claim 1 wherein both images are reconstructed simultaneously.

3. The method of claim 2 including the step of:
backprojecting 360 degrees of filtered projections, said backprojecting step is modified so that a projection is backprojected into one image for all pixel values before the focal-plane transition and into another image after the focal-plane transition, said focal-plane transition is defined to be the straight line through the scan origin at an angle equal to the angle of a projection being backprojected.

4. The method of claim 3 wherein smoothing is used in a region around the focal-plane transition.

5. The method of claim 4 wherein said smoothing step includes using weighted averages of the backprojected values from opposite directions.

6. The method of claim 1 wherein sectors are used instead of radial-lines.

7. The method of claim 6 wherein the sectors are overlapping.

8. The method of claim 7 wherein smoothing is used when combining overlapping sectors to form the images.

9. The method of claim 8 wherein said smoothing step includes using weighted averages of the portions of the sectors that overlap.

10. A correction method for minimizing artifacts caused by noncoplanarity between source means and detector means in computerized tomography, wherein said source means produces a beam of penetrating radiation which is rotatable about an axis and is incident on said detector means, whereby said noncoplanarity is defined by the collection of the positions of said source means which defines a first plane, and by the collection of the positions of said detector means which defines a second plane, said first and second planes being separated by a third plane that includes a portion of the object being scanned, said method including the steps of:
  (a) energizing said source means to provide radiation that passes from said source means to said detector means through an object when the latter is located between said source means and said detector means whereby output signals from the detector means are obtained;
  (b) processing said output signals to provide radiation intensity attenuation data of the object through 360 degrees; and
  (c) forming two images from the data, one image from the data related to one side of said third plane, and the second image from the data related to the other side of said third plane.

11. A system for mimimizing artifacts caused by noncoplanarity between source means and detector means in computerized tomography, wherein said source means produces a beam of penetrating radiation which is rotatable about an axis and is incident on said detector means, whereby said noncoplanarity is defined by the collection of the positions of said source means which defines a first plane, and by the collection of the positions of said detector means which defines a second plane axially displaced from said first plane, said system comprising:
  (a) means for energizing said source means to provide radiation that passes from said source means to said detector means through an object when the latter is located between said source means and said detector means whereby output signals from the detector means are obtained;
  (b) means for processing said output signals to form representations of line-integrals of the attenuation coefficients of the object;
  (c) means for processing said representations into filtered projection data over 360 degrees,
  (d) means for filtering the projection data; and
  means for obtaining two images by twice reconstructing a finite number of radial lines using a reconstruction algorithm, one reconstruction using the minimum filtered projection data required by the reconstruction algorithm centered about the angle of each radial line, and another reconstruction using the filtered projection data centered about the angle of the radial line plus 180 degrees.

12. The system of claim 11 wherein the last named means is constructed and arranged to reconstruct both images simultaneously.

13. The system of claim 12 including:
  means for backprojecting 360 degrees of filtered projections, said backprojecting means including means for backprojecting a projection into one image for all pixel values before the focal-plane transition and into another image after the focal-plane transition, said focal-plane transition is defined to be the straight line through the scan origin at an angle equal to the angle of a projection being backprojected.

14. The system of claim 13 wherein smoothing means are provided operating in a region around the focal-plane transition.

15. The system of claim 14 wherein said smoothing means comprise means for using weighted averages of the backprojected values from opposite directions.

16. The system of claim 11 wherein sectors are used instead of radial-lines.

17. The system of claim 16 wherein the sectors are overlapping.

18. The system of claim 17 wherein smoothing means are provided for combining overlapping sectors to form the images.

19. The system of claim 18 wherein said smoothing means includes means for using weighted averages of the portions of the sectors that overlap.

20. A system for minimizing artifacts caused by noncoplanarity between source means and detector means in computerized tomography, wherein said source means produces a beam of penetrating radiation which is rotatable about an axis and is incident on said detector means, whereby said noncoplanarity is defined by the collection of the positions of said source means which defines a first plane, and by the collection of the positions of said detector means which defines a second plane, said first and second planes being separated by a third plane that includes a portion of the object being scanned, said system comprising:
  (a) means for energizing said source means to provide radiation that passes from said source means to said detector means through an object when the latter is located between said source means and said detector means whereby output signals from the detector means are obtained;
  (b) means for processing said output signals to provide radiation intensity attenuation data of the object through 360 degrees; and
  (c) means for forming two images from the data, one image from the data related to one side of said third plane, and the second image from the data related to the other side of said third plane.

* * * * *